US011926853B2

(12) United States Patent
Yokouchi et al.

(10) Patent No.: US 11,926,853 B2
(45) Date of Patent: Mar. 12, 2024

(54) BOTULINUM TOXIN PRODUCING METHOD

(71) Applicant: The Research Foundation For Microbial Diseases of Osaka University, Suita (JP)

(72) Inventors: Daisuke Yokouchi, Kanonji (JP); Akiko Miura, Kanonji (JP); Ryu Okada, Kanonji (JP); Yuzo Yamashita, Kanonji (JP); Yuya Sasaki, Kanonji (JP); Shogo Nishihata, Kanonji (JP)

(73) Assignee: The Research Foundation For Microbial Diseases of Osaka University, Suita (JP)

( * ) Notice: Subject to any disclaimer, the term of this patent is extended or adjusted under 35 U.S.C. 154(b) by 180 days.

(21) Appl. No.: 17/416,342

(22) PCT Filed: Dec. 17, 2019

(86) PCT No.: PCT/JP2019/049436
§ 371 (c)(1),
(2) Date: Jun. 18, 2021

(87) PCT Pub. No.: WO2020/129986
PCT Pub. Date: Jun. 25, 2020

(65) Prior Publication Data
US 2022/0081682 A1 Mar. 17, 2022

(30) Foreign Application Priority Data
Dec. 21, 2018 (JP) .................. 2018-239214

(51) Int. Cl.
C12P 21/06 (2006.01)
C12N 9/52 (2006.01)

(52) U.S. Cl.
CPC ........ *C12N 9/52* (2013.01); *C12Y 304/24069* (2013.01)

(58) Field of Classification Search
CPC ....................................................... C12N 9/52
See application file for complete search history.

(56) References Cited

U.S. PATENT DOCUMENTS

| | | | |
|---|---|---|---|
| 5,173,418 A | 12/1992 | Molin et al. | |
| 2005/0238668 A1 | 10/2005 | Wang et al. | |
| 2005/0238669 A1 | 10/2005 | Xiang et al. | |
| 2011/0008843 A1 | 1/2011 | Ton et al. | |
| 2011/0092682 A1 | 4/2011 | Ruegg | |
| 2012/0108792 A1 | 5/2012 | Ton et al. | |
| 2012/0123095 A1 | 5/2012 | Ton et al. | |
| 2012/0156756 A1 | 6/2012 | Ton et al. | |
| 2012/0196349 A1 | 8/2012 | Ruegg | |
| 2012/0245324 A1 | 9/2012 | Ton et al. | |
| 2013/0171716 A1 | 7/2013 | Xiang et al. | |
| 2015/0184141 A1 | 7/2015 | Ton et al. | |
| 2015/0322419 A1 | 11/2015 | Ruegg | |
| 2015/0337281 A1 | 11/2015 | Kim et al. | |
| 2016/0097045 A1 | 4/2016 | Ton et al. | |
| 2017/0029795 A1 | 2/2017 | Ruegg | |
| 2017/0327811 A1 | 11/2017 | Ton et al. | |
| 2020/0071686 A1 | 3/2020 | Ton et al. | |
| 2020/0277591 A1 | 9/2020 | Ruegg | |

FOREIGN PATENT DOCUMENTS

| | | |
|---|---|---|
| CN | 105985968 A | 10/2016 |
| JP | 2008-531046 A | 8/2008 |
| JP | 2011-074025 A | 4/2011 |
| JP | 2012-532932 A | 12/2012 |
| JP | 2013-508388 A | 3/2013 |
| JP | 2016-521968 A | 7/2016 |
| KR | 10-1025617 B1 | 3/2011 |
| WO | WO 86/06743 A1 | 11/1986 |
| WO | WO 2006/096163 A1 | 9/2006 |

OTHER PUBLICATIONS

International Search Report in PCT/JP2019/049436 dated Mar. 17, 2020.
Emd Millipore, "Benzonase (R) endonuclease", [online], InternetT, Sep. 2018, 2018, pp. 1-40, https://www.emdmillipore.com/Web-US-Site/en CA/0/USD/ShowDocument-Pronet?id=201312.078, [retrieval date: Apr. 3, 2020 (Apr. 3, 2020)] examples 4-6.
Extended European Search Report for counterpart European Patent Application No. 19898205.0 dated Sep. 6, 2022.
Kitamura, M. et al., "Purification and Some Properties of *Clostridium botulinum* Type-E Toxin", *Biochim. et Biophys. Acta*, 168 (1968) 207-217.
Office Action issued for counterpart Japanese Patent Application No. 2020-561461, dated Oct. 17, 2023.
Chinese Office Action for Application No. 201980076236.4, dated Dec. 27, 2023 (in 17 pages).

*Primary Examiner* — Albert M Navarro
*Assistant Examiner* — Mark Navarro
(74) *Attorney, Agent, or Firm* — Knobbe Martens Olson & Bear LLP

(57) ABSTRACT

Provided is a *botulinum* toxin producing method which is simple achieves a high toxin yield, and obtains a toxin having high specific activity. This *botulinum* toxin producing method includes: (A) a step in which a *botulinum* toxin is produced from *botulinum* toxin-producing bacteria in a medium, and a mixture a is obtained which contains a *botulinum* toxin, a bacterial component, and a nucleic acid component derived from the *botulinum* toxin; (B) a step in which the mixture a is subjected to the removal of the bacterial component, and a mixture b is obtained which contains a nucleic acid component and a *botulinum* toxin; (C) a step in which an endonuclease is added to the mixture b and a mixture c is obtained which contains a nucleic acid degradation product and a *botulinum* toxin; and (D) a step in which the mixture c is subjected to removal of the nucleic acid degradation product, and an isolated *botulinum* toxin liquid d is obtained.

14 Claims, 4 Drawing Sheets

BOTULINUM TOXIN PRODUCING METHOD

TECHNICAL FIELD

The present invention relates to a method for producing a *botulinum* toxin.

BACKGROUND ART

The bacterium *Clostridium botulinum* (also referred to as a "*botulinum* bacterium", hereinafter) is a spore-forming obligate anaerobic gram-positive rod and can produce a neurotoxin (a *botulinum* toxin) capable of causing general paralysis. A *botulinum* toxin produced by the *botulinum* bacterium has the form of a complex composed of a neurotoxic component NTX and a non-toxic component bound to each other. The complex is classified into LL toxin (900 KDa), L toxin (500 KDa) or M toxin (300 KDa) depending on the molecular weight thereof. M toxin has such a structure that NTNH which is a non-toxic protein without a hemagglutination activity (a non-toxic non-HA protein) is bound to NTX, L toxin has such a structure that an HA protein which is non-toxic and has a hemagglutination activity is bound to M toxin, and LL toxin has such a structure that two molecules of L toxin are bound to each other. A toxin composed of only NTX is called "S toxin" (150 KDa). S toxin composed of only NTX can be isolated by subjecting a complexed toxin under alkaline conditions to dissociate NTX and NTNH from each other.

*botulinum* toxins are classified into any one of serotypes A to G, and *botulinum* toxins having the same serotype are classified into several subtypes depending on the difference in structures of toxin genes. For example, type-A *botulinum* bacteria are classified into type-A1 to type-A5 subserotypes. A type-A1 *botulinum* bacterium can produce LL toxin, L toxin and M toxin, while a type-A2 *botulinum* bacterium can produce only M toxin. Each of a type-B *botulinum* bacterium, a type-C *botulinum* bacterium and a type-D *botulinum* bacterium can produce LL toxin and M toxin. Each of a type-E *botulinum* bacterium and a type-F *botulinum* bacterium can produce only M toxin, while a type-G *botulinum* bacterium can produce only L toxin.

*botulinum* toxins have been used in clinical applications relying on the nerve-blocking activity thereof. Examples of the use applications of the *botulinum* toxins include post-stroke upper and lower limb spasticity, dystonia, hemifacial spasm, a sequela after a cerebrovascular disease and cosmetic surgery.

Due to the clinical usefulness of the *botulinum* toxins, various methods for producing a *botulinum* toxin from a *botulinum* bacterium have been proposed. In the methods for producing a *botulinum* toxin, a technique of treating a culture medium obtained after the culturing of a *botulinum* bacterium with an acid to cause acid precipitation of the *botulinum* toxin has been employed conventionally, and the improvements of the technique have been made. For example, Patent Document 1 discloses a method for purifying a non-complexed *botulinum* toxin, which includes: subjecting a fermentation culture containing a *botulinum* toxin to acid precipitation to produce acid precipitates, thereby producing a sample of the concentrated acid precipitates; subjecting the sample to nuclease digestion to produce a nuclease digestion product and then loading the nuclease digestion product over a hydrophobic interaction column to capture a complexed *botulinum* toxin; eluting and dissociating the complexed *botulinum* toxin to produce a mixture containing a crude non-complexed *botulinum* toxin; and applying the crude non-complexed *botulinum* toxin to an anion exchange column and a cation exchange column. Patent Document 2 discloses a method for producing a *botulinum* toxin, which includes the steps of: treating a liquid culture of a *botulinum* toxin-producing bacterium strain with an acid to cause the acid precipitation of a *botulinum* toxin; adding a buffer solution to the precipitated *botulinum* toxin and then extracting the *botulinum* toxin that is treated with a protease inhibitor and a nucleic acid degradation enzyme; treating the extracted *botulinum* toxin with an acid to cause the acid precipitation of the *botulinum* toxin, and then dissolving the resultant precipitates in a buffer solution; and purifying the *botulinum* toxin by employing anion exchange chromatography.

Meanwhile, in the methods for producing *botulinum* toxins, a technique in which acid precipitation as mentioned above is not carried out has also been employed. For example, Patent Document 3 discloses a process for producing a type-A *botulinum* neurotoxin complex, which includes the steps of: culturing and fermenting a *botulinum* bacterium; removing cell debris occurring in a fermentation culture medium to collect the fermentation culture medium; bringing the collected culture medium into contact with an anion exchange medium to capture a *botulinum* neurotoxin; and bringing an eluate eluted from the anion exchange medium into contact with a cation exchange medium. Patent Document 4 discloses a method for producing a *botulinum* toxin, which includes the steps of: removing cells of a *botulinum* bacterium from a liquid *botulinum* bacterium culture by a membrane filtration method; applying a *botulinum* toxin solution from which the cell of the *botulinum* bacterium have been removed over an anion exchange chromatography column; applying a collection fraction from the anion exchange chromatography column over a cation exchange chromatography column to eluate a *botulinum* toxin component to adsorb; and eluting the *botulinum* toxin.

PRIOR ART DOCUMENTS

Patent Documents

Patent Document 1: Japanese Translation of PCT International Application Publication No. 2013-508388

Patent Document 2: Japanese Translation of PCT International Application Publication No. 2016-521968

Patent Document 3: Japanese Translation of PCT International Application Publication No. 2012-532932

Patent Document 4: Japanese Patent Laid-open Publication No. 2011-74025

SUMMARY OF THE INVENTION

Problem to be Solved by the Invention

In the method for producing a *botulinum* toxin utilizing acid precipitation, a cell component (also referred to as a "bacterial component", hereinafter) and a nucleic acid component are co-precipitated in acid precipitates. The nucleic acid component can be fragmented by subjecting the acid precipitates to nuclease digestion. In this method, the bacterial cells are exposed to an acidic condition as the result of the acid precipitation to elute the toxin from the bacterial cells. In this case, the toxin is also precipitated together with the bacterial component and the nucleic acid component. The fragmented nucleic acid component and the cell component are removed by a purification operation employing chromatography as mentioned below or the like. However, in the technique employing acid precipitation, it is concerned about the following risks: the operation for the acid precipitation is complicated; a solution in which the fragmented nucleic acid component and the cell component (bacterial component) co-exist in a large quantity together with the *botulinum* toxin is subjected to purification, and therefore the separation by chromatography or the like is not sensitive and, consequently, separation performance becomes poor; an insoluble matter in which a large quantity of contaminants are co-precipitated is subjected to nuclease digestion, and therefore undigested nucleic acid may still remain; and others. On the other hand, in the method for producing a *botulinum* toxin without carrying out acid precipitation, the removal of nucleic acid is carried out employing anion exchange column chromatography. However, in the technique of remove nucleic acid removal by anion exchange column chromatography, both of the toxin and the nucleic acid are adsorbed onto an anion exchanger and therefore there is a limit in the yield of the toxin, and the specific activity of the yielded toxin is not still at a satisfactory level.

In these situations, the object of the present invention is to provide a method for producing a *botulinum* toxin, which is simple, can achieve a high toxin yield, and makes it possible to produce a toxin having a high specific activity.

Means for Solving the Problem

The present inventors have made extensive and intensive studies. As a result, it is found that a *botulinum* toxin having a high specific activity can be produced with high toxin yield without the need to employ acid precipitation or anion exchange chromatography for nucleic acid removal purpose, by applying a nuclease treatment, which has been applied only to acid precipitates in which a bacterial component co-exists unavoidably together with a *botulinum* toxin so far, to a *botulinum* toxin mixture prepared by removing the bacterial component from a *botulinum* bacterium culture fermented product. The present invention has been accomplished by further repeating the studies on the basis of this finding.

The present invention provides the following aspects of inventions.

Item 1. A method for producing a *botulinum* toxin, including steps of:

(A) producing a *botulinum* toxin from a *botulinum* toxin-producing bacterium in a culture medium to produce a mixture a containing a bacterial component and a nucleic acid component both derived from the *botulinum* toxin and the *botulinum* toxin;

(B) subjecting the mixture a to the removal of the bacterial component to produce a mixture b containing the nucleic acid component and the *botulinum* toxin;

(C) adding an endonuclease to the mixture b to produce a mixture c containing a nucleic acid degradation product and the *botulinum* toxin; and (D) subjecting the mixture c to the removal of the nucleic acid degradation product to produce an isolated *botulinum* toxin liquid d.

Item 2. The method for producing a *botulinum* toxin according to item 1, wherein, in the step (C), the endonuclease is an endonuclease derived from a *Serratia* bacterium *Serratia marcescens*.

Item 3. The method for producing a *botulinum* toxin according to item 1 or 2, wherein the step (C) is carried out under the condition of pH 5.8 to 6.5.

Item 4. The method for producing a *botulinum* toxin according to any one of items 1 to 3, wherein, in the step (C), the endonuclease is added a plurality of times.

Item 5. The method for producing a *botulinum* toxin according to any one of items 1 to 4, wherein, in the step (D), the removal of the nucleic acid degradation product includes the removal using a membrane.

Item 6. The method for producing a *botulinum* toxin according to any one of items 1 to 5, wherein the method further includes a step (E) of subjecting the isolated *botulinum* toxin liquid d to cation exchange chromatography to produce a purification product of a complexed *botulinum* toxin.

Item 7. The method for producing a *botulinum* toxin according to item 6, wherein the method further includes a step (F) of subjecting the purification product of the complexed *botulinum* toxin to anion exchange chromatography under a condition where a non-toxic non-HA protein can be dissociated from the complexed *botulinum* toxin to produce a purification product of a non-complexed *botulinum* toxin.

Item 8. The method for producing a *botulinum* toxin according to any one of items 1 to 7, wherein at least the step (A) includes a preculture step and a main culture step and at least the preculture step is carried out by static culture.

Item 9. The method for producing a *botulinum* toxin according to any one of items 1 to 8, wherein both of the preculture step and the main culture step are carried out by static culture.

Item 10. The method for producing a *botulinum* toxin according to item 8 or 9, wherein the step (A) includes the following steps in this order:

(A1) carrying out the bacterial growth of the *botulinum* toxin-producing bacterium in a culture medium of pH 6.8 to 8.0; and (A2) carrying out the fermentation of the *botulinum* toxin-producing bacterium in a culture medium of pH 5.0 to 6.5.

Item 11. The method for producing a *botulinum* toxin according to any one of items 1 to 10, wherein, in the step (A), the *botulinum* toxin-producing bacterium is a germinated body of a cell which is stored in the form of a spore.

Item 12. The method for producing a *botulinum* toxin according to any one of items 1 to 11, wherein, in the step (B), the removal of the bacterial component includes filter filtration.

Item 13. The method for producing a *botulinum* toxin according to any one of items 7 to 12, wherein, in the step (F), the condition includes pH 7.3 to 8.5.

Item 14. The method for producing a *botulinum* toxin according to any one of items 7 to 13, wherein, in the step (F), the anion exchange chromatography is carried out by weak anion exchange chromatography.

Item 15. A purified *botulinum* toxin characterized by having a specific activity of $3.0 \times 10^7$ U/mg or more.

Item 16. A purified *botulinum* toxin produced by a method for producing a *botulinum* toxin as recited in any one of items 1 to 14.

Advantages of the Invention

According to the present invention, the production of a *botulinum* toxin becomes possible, which is simple, has high toxin yield, and makes it possible to produce a toxin having a high specific activity.

BRIEF DESCRIPTION OF DRAWINGS

FIG. 1 is stained image of electrophoresis gel which shows the purification of a *botulinum* toxin in Example 1.

FIG. 2 is stained image of electrophoresis gel which shows the purification of a *botulinum* toxin in Comparative Example 1.

FIG. 3 is stained image of electrophoresis gel which shows the purification of a *botulinum* toxin in Example 2.

FIG. 4 is stained image of electrophoresis gel which shows the purification of a *botulinum* toxin in Example 3.

EMBODIMENTS OF THE INVENTION

The method for producing a *botulinum* toxin according to the present invention includes steps of:

(A) producing a *botulinum* toxin from a *botulinum* toxin-producing bacterium in a culture medium to produce a mixture a containing a bacterial component and a nucleic acid component both derived from the *botulinum* toxin and the *botulinum* toxin;

(B) subjecting the mixture a to the removal of the bacterial component to produce a mixture b containing the nucleic acid component and the *botulinum* toxin;

(C) adding an endonuclease to the mixture b to produce a mixture c containing a nucleic acid degradation product and the *botulinum* toxin; and (D) subjecting the mixture c to the removal of the nucleic acid degradation product to produce an isolated *botulinum* toxin liquid d. The method for producing a *botulinum* toxin according to the present invention may further include a step (E) of subjecting the isolated *botulinum* toxin liquid d to cation exchange chromatography to produce a purification product of a complexed *botulinum* toxin (i.e., a *botulinum* toxin in the form of a complex), or a step (F) of subjecting the purification product of the complexed *botulinum* toxin to anion exchange chromatography under a condition where a non-toxic non-HA protein can be dissociated from the complexed *botulinum* toxin to produce a purification product of a non-complexed *botulinum* toxin (i.e., a *botulinum* toxin in a non-complexed form).

The serotype of the *botulinum* toxin in the present invention includes type-A, type-B, type-C, type-D, type-E, type-F and type-G serotypes. The type of the *botulinum* toxin includes a complexed *botulinum* toxin and a non-complexed *botulinum* toxin. The complexed *botulinum* toxin complex includes LL toxin (900 KDa), L toxin (500 KDa) and M toxin (300 KDa). The non-complexed *botulinum* toxin refers to S toxin (150 KDa) which is composed only of NTX. NTX has a double-stranded fragment structure in which a 50-KDa light chain and a 100-KDa heavy chain are bonded to each other through disulfide bonds.

(A) Production of *botulinum* Toxin from *botulinum* Toxin-Producing Bacterium

In the step (A), a *botulinum* toxin is produced from a *botulinum* toxin-producing bacterium in a culture medium to produce a mixture a containing a bacterial component and a nucleic acid component both derived from the *botulinum* toxin and the *botulinum* toxin.

The *botulinum* toxin produced in this step includes a naturally occurring *botulinum* toxin and a modified *botulinum* toxin. The term "modified *botulinum* toxin" refers to a *botulinum* toxin having such a structure that at least one of the amino acid residues is deleted, modified, added, inserted or substituted compared with the naturally occurring *botulinum* toxin. The modified *botulinum* toxin may be a recombinantly produced neurotoxin. The modified *botulinum* toxin is only required to have at least one of biological activities of naturally occurring *botulinum* toxin, such as an ability to bind to a *botulinum* toxin receptor and an ability to inhibit the release of a neurotransmitter from a neuron. An example of the modified *botulinum* toxin is a *botulinum* toxin which has a light chain derived from a *botulinum* toxin serotype (e.g., serotype A) and a heavy chain derived from a *botulinum* toxin serotype (e.g., serotype B) that is different from the aforementioned *botulinum* toxin serotype. In this step, a single type of *botulinum* toxin may be produced, or a plurality of *botulinum* toxins may be produced. From the viewpoint of purification efficiency and the like, it is preferred that a single type of *botulinum* toxin is produced.

The *botulinum* toxin-producing bacterium (also referred to as a "*botulinum* bacterium", hereinafter) may be any one, as long as the bacterium can produce the above-mentioned *botulinum* toxin. Examples of the *botulinum* toxin-producing bacterium include *Clostridium botulinum* and a recombinant thereof. More specific examples of the *botulinum* toxin-producing bacterium include a type-A1 *botulinum* bacterium which can produce LL toxin, L toxin and M toxin; a type-A2 *botulinum* bacterium which can produce only M toxin; type-B, type-C and type-D *botulinum* bacteria each of which can produce LL toxin and M toxin; type-E and type-F *botulinum* bacteria each of which can produce only M toxin; and a type-G *botulinum* bacterium which can produce only L toxin. The *botulinum* toxin-producing bacterium is preferably type-A2, type-E and type-F *botulinum* bacteria each of which can produce only M toxin, more preferably a type-A2 *botulinum* bacterium. The type-A2 *botulinum* bacterium strain is specifically a pathogenic bacterium of infant botulism, more specifically Kyoyo-F, Chiba-H, Y-8036, 7I03-H, 7I05-H, KZ1828 or the like, preferably Chiba-H. The *botulinum* toxin-producing bacterium is preferably a germinated body of a *botulinum* bacterium which is stored in the form of a spore. The *botulinum* toxin-producing bacterium can be improved in the stability for use as a seed strain, and can produce a toxin efficiently.

As the method for producing a *botulinum* toxin from the *botulinum* toxin-producing bacterium in a culture medium, any method may be employed. For example, the method of Sakaguchi et. al. (Sakaguchi G., Biomedical aspects of botulism: Purification and oral toxicities of *Clostridium botulinum* progenitor toxins., 21-34, Lewis G E., 1981, Academic Press, New York) can be mentioned. The step (A) may include a preculture step and a main culture step. Preferably, the preculture step can be carried out by static culture, and the main culture step can be carried out by agitation culture or static culture. More preferably, both of the preculture step and the main culture step can be carried out by static culture.

The preculture step is a step of carrying out the expansion culture of bacterial cells, and the main culture step is a step of carrying out the culture for producing bacterial cells. It is preferred that the main culture step includes a step (A1) of carrying out the bacterial growth of the *botulinum* toxin-producing bacterium and a step (A2) of carrying out the fermentation of the *botulinum* toxin-producing bacterium in this order. In the step (A2), both of the elution of the *botulinum* toxin (bacteriolysis) and the bacterial growth proceed.

From the viewpoint of the more satisfactory proceeding of the bacterial growth, the pH of the culture medium in the step (A1) is preferably 6.8 to 8.0. More specifically, it is possible to prepare a culture medium that is adjusted to pH 7.0 to 8.0, preferably pH 7.1 to 8.0, more preferably pH 7.2 to 8.0, still more preferably pH 7.2 to 7.8, and start the step (A1) using the culture medium.

From the viewpoint of the more satisfactory proceeding of both of the elution of the *botulinum* toxin (bacteriolysis) and the bacterial growth, the pH of the culture medium in the step (A2) is preferably 5.0 to 6.5.

As one example of the method for adjusting the pH to the above-mentioned pH in the step (A2), a method in which the pH is decreased artificially by adding a pH modifier to the culture medium in the step (A2) can be mentioned. The operation for decreasing the pH artificially can be carried out after the confirmation that the bacterial growth by the step (A1) reaches the peak thereof. The method for decreasing the pH artificially is carried out preferably in the case where agitation culture is employed.

As another example of the method for adjusting the pH to the above-mentioned pH in the step (A2), a method in which a phenomenon that the pH decreases spontaneously is utilized in the step (A1) without the need to control the pH artificially can be mentioned. The adjustment utilizing the phenomenon that the pH decreases spontaneously can be carried out preferably in the case where static culture is employed. When the step (A1) is allowed to move to the step (A2) by utilizing the spontaneous decrease of the pH, the confirmation that the step (A) proceeds and is completed can be carried out by confirming that the pH of the culture medium decreases preferably to 5.5 to 6.5.

The culture medium to be used in the step (A) is not particularly limited, and may be selected appropriately by a person skilled in the art. Preferably, the culture medium contains at least either one of a vegetable peptone and an animal-derived peptone. The vegetable peptone is a degradation product of a protein produced from a vegetable. Examples of the vegetable peptone include peptones derived from pea, soybean, cotton seed, wheat gluten and the like. The vegetable peptone is preferably a peptone derived from pea. The animal-derived peptone is a degradation product of a protein derived from an animal tissue. Examples of the animal-derived peptone include peptones derived from pig, cow, sheep and the like. The animal-derived peptone is preferably a peptone derived from pig. The total content of the vegetable peptone and the animal-derived peptone in the culture medium to be used in the preculture step is, for example, 1 to 12 w/v %, preferably 2 to 10 w/v %. The total content of the vegetable peptone and the animal-derived peptone in the culture medium to be used in the main culture step is preferably smaller than that in the culture medium to be used in the preculture step, and is, for example, 0.1 to 5 w/v %, preferably 1 to 3 w/v %. In the present description, the unit "w/v %" refers to a mass-volume percentage as prescribed in The Japanese Pharmacopoeia, Seventeenth Edition.

The culture medium may further contain a carbon source and a culture medium reducing agent. Examples of the carbon source include a monosaccharide (e.g., glucose, fructose), a disaccharide (e.g., maltose, sucrose), an oligosaccharide, a polysaccharide (e.g., dextrin, cyclodextrin, starch), and a sugar alcohol (e.g., xylitol, sorbitol, erythritol). The carbon source is preferably a monosaccharide, more preferably glucose. Examples of the culture medium reducing agent include sodium thioglycolate, cysteine and sodium L-ascorbate. The culture medium reducing agent is preferably sodium thioglycolate.

In the culture medium at the time point of the completion of the step (A), the *botulinum* toxin produced from the *botulinum* toxin-producing bacterium co-exists together with a bacterial component and a nucleic acid component both derived from the *botulinum* toxin-producing bacterium. Therefore, by the step (A), a mixture a containing a bacterial component and a nucleic acid component both derived from the *botulinum* toxin-producing bacterium and the *botulinum* toxin is produced. In the mixture a, a culture medium component is also contained in addition to the bacterial component, the nucleic acid component and the *botulinum* toxin.

(B) Removal of Bacterial Component

In the step (B), the mixture a produced in the step (A) is subjected to the removal of the bacterial component to produce a mixture b containing the nucleic acid component and the *botulinum* toxin. In the present invention, a technique for causing the bacterial component and the nucleic acid component to precipitate together with the *botulinum* toxin from the mixture a, such as acid precipitation, is not carried out, or a technique for removing the nucleic acid component previously is not carried out, either. Therefore, in the present invention, a complicated operation like a precipitation treatment such as acid precipitation is not needed. Furthermore, because acid precipitation is not carried out, the loss of the *botulinum* toxin is reduced and, therefore, an excellent yield can be achieved. Furthermore, because the *botulinum* toxin is not exposed to a strongly acidic condition, the toxic activity of the *botulinum* toxin can be kept satisfactorily. In the present invention, the addition of any nuclease to the mixture a is not carried out before the removal of the bacterial component by the step (B).

The technique for removing the bacterial component is not particularly limited. More specifically, the technique may be one which has a bacterial component separation ability that is at the same level or higher as or than that achieved in an eluate obtained in the case where the mixture is filtrated through a filter having a pore diameter of 0.22 µm or less. That is, in the present invention, the removal accuracy in the removal of the bacterial component is only required to be at the same level or higher as or than that achieved in the case where a filter having a pore diameter of 0.22 µm or less is used.

More specific examples of the technique for removing the bacterial component include filter filtration, centrifugation and membrane filtration. The technique is preferably filter filtration. The pore diameter of the filter to be used in the filter filtration is, for example, 10 µm or less. The filter filtration may be carried out in a plurality of stages in such a manner that filters having different pore diameters are used and the pore diameters of the filters through which a solution of interest is passed become smaller stepwise. In this case, the filter filtration may be carried out in 2 to 4 stages, preferably 3 to 4 stages. When the filter filtration is carried out in a plurality of stages, the pore diameter of a filter to be used in the final stage is preferably 0.22 µm or less from the viewpoint of achieving the more precise removal of the bacterial component. Examples of the material for the filter to be used include cellulose, perlite, a resin, diatomaceous earth, polyethersulfone, cellulose acetate and polyvinylidene difluoride.

The component to be removed in the step (B) is primarily the bacterial component. In the step (B), the nucleic acid component may also be removed partly together with the bacterial component. When the filter filtration is carried out, the bacterial component is left on the filter and an eluate is collected as the mixture b.

In this manner, by removing the bacterial component from the mixture a, the mixture b containing the nucleic acid component and the *botulinum* toxin can be produced. The mixture b may also be produced in an appropriately concentrated form. For example, the mixture b may be produced by further concentrating an eluate that has passed through the filter. The technique for the concentration is not particularly limited, and is, for example, concentration with a membrane. In this case, it is preferred to use an ultrafiltration membrane to perform buffer exchange with a buffer capable of dissolving the *botulinum* toxin, such as a phosphate buffer and an MES buffer. The pore diameter (molecular weight cut-off) of the ultrafiltration membrane is, for example, 20 to 40 KDa, preferably 25 to 35 KDa.

The mixture b can be obtained as a substantially clear liquid from which the bacterial component is removed. More preferably, the mixture b can be obtained in a form that contains the nucleic acid component and the *botulinum* toxin together with the buffer. The mixture b may also contain the culture medium component.

(C) Treatment With Endonuclease

In the step (C), an endonuclease is added to the mixture b to produce a mixture c containing a nucleic acid degradation product and the *botulinum* toxin. As mentioned above, in the present invention, any technique for causing the bacterial component and the nucleic acid component to precipitate together with the *botulinum* toxin, e.g., acid precipitation, which has been employed often in the production of a *botulinum* toxin, is not carried out. Firstly, in order to remove the nucleic acid component, an endonuclease is added to the mixture b from which the bacterial component has been removed previously. The nucleic acid component in the mixture b is fragmented by the action of the endonuclease to produce a nucleic acid degradation product. As a result, it becomes possible to remove the nucleic acid degradation product (i.e., remove nucleic acid species in such a manner that the quantity of the nucleic acid species remaining in the mixture can be smaller) with a superior efficiency in the below-mentioned step (D) without the need to employ anion exchange column chromatography. In the present invention, because the bacterial component is removed previously from the mixture b, the endonuclease can act on the nucleic acid component more effectively without being interfered with the bacterial component. Therefore, it also becomes possible to fragment the nucleic acid component efficiently while reducing remaining undigested nucleic acids. This matter can also contribute to the removal of a nucleic acid degradation product with superior efficiency in the below-mentioned step (D).

As the endonuclease, an enzyme having an endonuclease activity can be used without any particular limitation. Examples of the nucleic acid component that is a substrate for the endonuclease include DNA and RNA. Therefore, the endonuclease is preferably an enzyme capable of degrading both of DNA and RNA. Specific examples of the endonuclease include an endonuclease derived from a *Shewanella* sp. bacterium, an endonuclease derived from *Staphylococcus aureus*, and an endonuclease derived from a *Serratia* bacterium *Serratia marcescens*. Among these endonucleases, an endonuclease derived from a *Serratia* bacterium is particularly preferred.

Specific examples of the endonuclease derived from a *Serratia* bacterium include Benzonase (Merck KGaA, registered trademark), Denarase (c-LEcta GmbH, registered trademark) and Kaneka endonuclease (Kaneka Corporation), preferably Benzonase and Denarase, more preferably Benzonase. The optimum pH of the endonuclease derived from a *Serratia* bacterium is higher compared with the common endonucleases, and is specifically about 7.5 to 9.2. More specifically, the optimum pH of Benzonase is 8.0 to 9.2, the optimum pH of Denarase is 8.0 to 9.0, and the optimum pH of Kaneka endonuclease is 7.5 to 9.0.

In the step (C), from the viewpoint of preventing the dissociation and/or degradation of the *botulinum* toxin, it is preferred to allow the endonuclease to act under the condition of pH 5.8 to 6.5, more preferably pH 5.9 to 6.3. When the endonuclease derived from a *Serratia* bacterium which is mentioned as a preferred endonuclease is used, it is also preferred to allow the endonuclease to act under the above-mentioned pH condition, although the pH is greatly out of the optimum pH of the endonuclease. In the present invention, even when an endonuclease derived from a *Serratia* bacterium is allowed to act under the condition of pH 5.8 to 6.5, it also becomes possible to remove the nucleic acid component efficiently in the below-mentioned step (D).

In the step (C), the number of times to add the endonuclease to the mixture b is not particularly limited, and may be once or a plurality of times. When an endonuclease derived from a *Serratia* bacterium is used, it is preferred to add the endonuclease a plurality of times from the viewpoint of achieving more efficient fragmentation of the nucleic acid. Preferably, the endonuclease may be added two to four times, more preferably two to three times. When the endonuclease is added a plurality of times, the timing of the addition of the endonuclease is not particularly limited. For example, the endonuclease may be added at 1- to 12-hour intervals, preferably 2- to 9-hour intervals, more preferably 3- to 7-hour intervals. The temperature at which the endonuclease is allowed to act is, for example, 25 to 40° C., preferably 28 to 38° C. The total time required for the endonuclease treatment is, for example, 10 to 24 hours, preferably 12 to 20 hours. When an endonuclease derived from a *Serratia* bacterium is used, a series of process from the step (C) to the below-mentioned step (D) may be repeated a plurality of times. In this case, the number of times to add the endonuclease to the mixture b in the step (C) in a single process is preferably once. When a series of process from the steps (C) to (D) is repeated, a specific example of the number of repeating times is, for example, 2 to 4 times, preferably 2 to 3 times. For example, when the series of process is repeated 2 times, the present invention includes the steps (A), (B), (C), (D), (C) and (D) in this order.

In this manner, by treating the mixture b with the endonuclease, a mixture c containing a nucleic acid degradation product and the *botulinum* toxin can be produced. If necessary, the mixture c may be obtained as a filtrate which has been undergone a filtration treatment such as filter filtration for the purpose of removing nucleic acid that cannot be still degraded or other purposes. More specifically, the mixture c may be obtained in a form which contains an endonuclease residue and a buffer together with the nucleic acid degradation product and the *botulinum* toxin. The mixture c may also contain the above-mentioned culture medium component.

(D) Removal of Nucleic Acid Degradation Product

In the step (D), the mixture c is subjected to the removal of a nucleic acid degradation product to produce an isolated *botulinum* toxin liquid d. The technique for removing the nucleic acid degradation product is not particularly limited, as long as the nucleic acid degradation product can be separated from the *botulinum* toxin. However, an anion exchanger is not used. When an anion exchanger is used, there is a limitation in toxin yield. Therefore, even in the case where both of the toxin and the nucleic acid species are captured firstly and the toxin is then eluted by pH gradient elution as well as the case where only the nucleic acid species is captured and the toxin is eluted without being captured, the collection of the toxin is insufficient. Furthermore, when an anion exchanger is used, it is impossible to produce a toxin having a sufficient specific activity. Furthermore, when an anion exchanger is used, the time required for the operation by an operator becomes long and, therefore, the chances for contamination may increase. For these reasons, in the present invention, any anion exchanger is not used for the removal of the nucleic acid degradation product from the viewpoint of the yield of the toxin, the specific activity of the toxin, operability and the like.

In the present invention, any treatment for causing the bacterial component and the nucleic acid component to precipitate together with the *botulinum* toxin from the mixture a, e.g., acid precipitation, is not carried out and the remaining nucleic acid component is degraded after the removal of cells. Therefore, in a substance to be subjected to the separation of the *botulinum* toxin (i.e., the mixture c in the present invention), the quantity of contaminants to be removed is reduced and the molecular weights of the contaminants are also reduced. As a result, the removal of the contaminants (i.e., the nucleic acid degradation product) can be carried out with satisfactory separation performance.

As the technique for removing the nucleic acid degradation product, any means for separating the nucleic acid degradation product from the *botulinum* toxin can be employed without any limitation, as long as no anion exchanger is used. A more specific example of the technique for the removal is the removal through a membrane, preferably the filtration through a membrane (i.e., membrane filtration). In this manner, a low-molecular-weight substance, e.g., the nucleic acid degradation product, can pass through a membrane, and can be separated from the *botulinum* toxin that cannot pass through the membrane. The pore diameter of the membrane to be used for the removal through a membrane is, for example, 20 to 40 KDa, preferably 25 to 35 KDa, in terms of molecular weight cut-off. As a membrane separator liquid, a buffer capable of dissolve the *botulinum* toxin, e.g., a phosphate buffer and an acetate buffer, can be used preferably.

In this manner, by removing the nucleic acid degradation product from the mixture c, an isolated *botulinum* toxin liquid d from which contaminants such as nucleic acid have been removed satisfactorily can be obtained. The *botulinum* toxin in the isolated *botulinum* toxin liquid d is produced in a form that is the same as the form produced in the step (A). For example, when a type-A1 *botulinum* bacterium is used as a *botulinum* toxin-producing bacterium in the step (A), the *botulinum* toxin in the isolated *botulinum* toxin liquid d produced in the step (D) is contained in the forms of LL toxin, L toxin or M toxin. When a type-A2 *botulinum* bacterium is used as the *botulinum* toxin-producing bacterium in the step (A), the *botulinum* toxin in the isolated *botulinum* toxin liquid d produced in the step (D) is contained in the form of M toxin. The isolated *botulinum* toxin liquid d can be produced in the form of a clear liquid. More preferably, the isolated *botulinum* toxin liquid d can be produced in a form in which the *botulinum* toxin is contained together with the buffer. The isolated *botulinum* toxin liquid d may still contain the culture medium component.

The isolated *botulinum* toxin liquid d may be subjected to an optional purification step for purifying the *botulinum* toxin. The technique for the *botulinum* toxin purification is not particularly limited, and can be selected by a person skilled in the art appropriately depending on the types of the *botulinum* toxin. From the viewpoint of achieving excellent purity, the technique is the purification by column chromatography, more preferably the purification by ion exchange column chromatography. The specific technique for the ion exchange column chromatography may be selected appropriately depending on the types of the pH dependency of the *botulinum* toxin. The *botulinum* toxin has the property of forming a cation under an acidic condition preferably at pH 4.0 to 5.0, preferably about pH 4.0, and forming an anion at pH 7.0 or higher, preferably about pH 7.5. The complexed *botulinum* toxin has the property of existing stably in the form of a complex under a weakly acidic condition preferably at pH 5.5 to 6.5, preferably about pH 6.0, and being dissociated into a non-complexed form with the increase in pH to, for example, pH 7.3 to 8.0. Preferably, the purification of the *botulinum* toxin includes the purification of a complexed *botulinum* toxin by the below-mentioned step (E) or the purification of a non-complexed *botulinum* toxin by the below-mentioned step (F).

(E) Purification of Complexed *botulinum* Toxin

In the step (E), the isolated *botulinum* toxin liquid d is subjected to cation exchange chromatography to produce a purification product of a complexed *botulinum* toxin. The complexed *botulinum* toxin can form a cation under an acidic condition. Therefore, the purification by cation exchange chromatography is superior because the complexed *botulinum* toxin can be captured and purified stably. The purification by cation exchange chromatography is also superior because the purification can be achieved under such a pH condition that the dissociation of the complexed *botulinum* toxin can be inhibited.

The cation exchanger can be equilibrated in advance with a buffer preferably of pH 4.0 to 4.5, more specifically pH 4.2. The salt concentration in the buffer for the equilibration is, for example, 0.3 mol/L or less, preferably 0.2 mol/L or less, more specifically 0.2 mol/L. The type of the buffer is not particularly limited. Examples of the buffer include an acetate buffer, a succinate buffer, a citrate buffer, a formate buffer and a barbiturate buffer, preferably an acetate buffer. By applying the isolated *botulinum* toxin liquid d to the equilibrated cation exchanger, the *botulinum* toxin (the complexed *botulinum* toxin) can be captured by the cation exchanger.

The elution of the captured *botulinum* toxin (complexed *botulinum* toxin) can be carried out by flowing a buffer that is the same as the buffer for equilibration use under a gradient condition from a salt concentration of the buffer for equilibration use to, for example, 0.5 to 0.8 mol/L, more specifically 0.7 mol/L. In this manner, the purified complexed *botulinum* toxin can be obtained as an eluate.

The cation exchanger is not particularly limited. An example of the cation exchanger is a commercially available cation exchange resin such as SP Sepharose Fast Flow (GE Healthcare), CM Sepharose Fast Flow (GE Healthcare), S Sepharose Fast Flow (GE Healthcare) and SP Toyopearl (Tosoh Corporation). The type of the salt in the buffer is not limited, and the salt may be used at such a concentration that the ionic strength can correspond to that of sodium chloride at the above-mentioned concentration. A preferred example of the salt in the buffer is sodium chloride.

In this manner, the complexed *botulinum* toxin can be produced by the purification employing cation exchange chromatography. If necessary, the complexed *botulinum* toxin may be adjusted to pH 5.5 to 6.5, more specifically pH 6.0, for the purpose of stabilizing the complexed *botulinum* toxin. If necessary, the complexed *botulinum* toxin may be produced in a form which has been subjected to a treatment such as concentration and filtration. Specific technique for the concentration may be selected from the techniques mentioned in the step (B). Specific examples of the technique of the filtration include techniques employed for the purpose of sterilization or final filtration, such as a technique using a filter having a pore diameter of, for example, 0.15 to 0.3 μm, more specifically 0.22 μm. When it is intended to provide a *botulinum* toxin preparation in the form of the complexed *botulinum* toxin, an additive such as a preservative agent may be blended prior to the filtration.

(F) Purification of Non-Complexed *botulinum* Toxin

In the step (F), the purified product of the complexed *botulinum* toxin is subjected to anion exchange chromatography under a condition where a non-toxic non-HA protein can be dissociated from the complexed *botulinum* toxin to produce a purification product of a non-complexed *botulinum* toxin.

The purification product of the complexed *botulinum* toxin may be subjected to a condition where the non-toxic non-HA protein can be dissociated from the complexed *botulinum* toxin prior to the anion exchange chromatography. The condition where the non-toxic non-HA protein can be dissociated from the complexed *botulinum* toxin preferably includes pH 7.3 to 8.5, more preferably pH 7.4 to 8.0, specifically pH 7.5. The temperature is preferably 10° C. or lower. More specifically, the non-toxic non-HA protein can be dissociated using an ultrafiltration membrane by the buffer exchange with a buffer (e.g., phosphate buffer, Tris buffer, HEPES buffer; preferably a phosphate buffer) which is adjusted to the above-mentioned pH and has a salt concentration of 0.1 mol/L or less, preferably 0.05 mol/L or less. The pore diameter (molecular weight cut-off) of the ultrafiltration membrane is 5 to 30 KDa, preferably 8 to 20 KDa, more preferably 9 to 15 KDa.

The anion exchanger can be equilibrated in advance with a buffer which is adjusted to a condition where the non-toxic non-HA protein can be dissociated from the complexed *botulinum* toxin (preferably pH 7.3 to 8.5, specifically pH 7.5). The salt concentration in the buffer to be used for the equilibration is 0.1 mol/L or less, preferably 0.05 mol/L or less. The type of the buffer is not particularly limited. Examples of the buffer include a phosphate buffer, Tris buffer and HEPES buffer, preferably a phosphate buffer. The purification product of the complexed *botulinum* toxin or a treatment product thereof which is produced by subjecting the purification product to a condition where the non-toxic non-HA protein can be dissociated is applied to the equilibrated anion exchanger. As a result, a *botulinum* toxin which is anionized due to the pH of the contacted environment (i.e., a non-complexed *botulinum* toxin) can be captured.

The elution of the captured non-complexed *botulinum* toxin can be carried out using a buffer that is the same as the buffer for equilibration use under a gradient condition from a salt concentration in the buffer for equilibration use to, for example, 0.1 to 0.5 mol/L, preferably 0.2 to 0.4 mol/L, more specifically 0.3 mol/L. In this manner, a purified non-complexed *botulinum* toxin can be obtained as an eluate.

In this case, the dissociated non-toxic non-HA protein can also be captured on the exchanger. The non-toxic non-HA protein can be separated from the non-complexed *botulinum* toxin by a technique utilizing the difference in their own elution timings in the gradient of the salt concentration in a mobile phase or the like.

The anion exchanger is not particularly limited. From the viewpoint of making the elution of the non-complexed *botulinum* toxin easier to thereby make the separation between the non-complexed *botulinum* toxin and the dissociated non-toxic non-HA protein easier, the anion exchanger is preferably a weak anion exchanger. Examples of the anion exchanger include commercially available anion exchange resins, such as DEAE Sepharose Fast Flow (GE Healthcare), DEAE Toyopearl (Tosoh Corporation), Diaion WA10 (Mitsubishi Chemical Corporation) and Fractogel DEAE (Merck KGaA). The type of the salt in the buffer is not limited, and the salt may be used at such a concentration that the ionic strength can correspond to that of sodium chloride at the above-mentioned concentration. A preferred example of the salt in the buffer is sodium chloride.

In this manner, the non-complexed *botulinum* toxin can be produced by the purification employing anion exchange chromatography. If necessary, the non-complexed *botulinum* toxin may be produced in a form which has been subjected to a treatment such as concentration and filtration. For the purpose of providing the non-complexed *botulinum* toxin as a *botulinum* toxin preparation, an additive such as a preservative agent may be further blended. Specific technique for the concentration or the filtration may be selected from the techniques mentioned in the step (E).

Purified *botulinum* Toxin

The purified product of the *botulinum* toxin (also referred to as "purified *botulinum* toxin", hereinafter) which is produced by the method of the present invention has an excellent specific activity. Specific example of the specific activity is $3.0 \times 10^7$ U/mg or more, preferably $4.0 \times 10^7$ U/mg or more, more preferably $5.0 \times 10^7$ U/mg or more, still more preferably $6.0 \times 10^7$ U/mg or more, further preferably $7.0 \times 10^7$ U/mg or more, still further preferably $8.0 \times 10^7$ U/mg or more, especially preferably $9.0 \times 10^7$ U/mg or more, most preferably $10.0 \times 10^7$ U/mg or more.

The term "specific activity" as used herein refers to a titer (U/mg) per 1 mg of a protein. The term "titer" as used herein refers to a lethal activity (i.e., an LD50 value in the case of intraperitoneal administration) in a mouse which is calculated by a mouse intraperitoneal administration method, wherein 1 U=1 LDS50. The titer may also be calculated by a mouse tail vein administration method. The method for measuring the titer of the purified *botulinum* toxin by the mouse tail vein administration method is an alternative method of the commonly employed mouse intraperitoneal administration method, and is a method in which a high concentration of the purified *botulinum* toxin is administered to a tail vein of a mouse to determine the survival time of the mouse and the titer is calculated from a regression line of the survival time of the mouse which has been verified in advance and a LD50 value obtained in the case of intraperitoneal administration. A protein can be measured by an ultraviolet absorption measurement method (280 nm), Lowry method, BCA method or the like. As a specific example of the method for measuring the specific activity in the case where the *botulinum* toxin is produced in the form of a liquid (i.e., a *botulinum* toxin liquid), the LD50 value (U) per 1 mL of the *botulinum* toxin liquid is measured and the specific activity can be determined by dividing a measurement value thus obtained by the mass (mg) of a protein in 1 mL of the *botulinum* toxin liquid.

(E) *botulinum* Toxin Preparation

The purified *botulinum* toxin produced by the production method of the present invention is useful as an active ingredient for a *botulinum* preparation. The use applications of the *botulinum* preparation include all clinical applications, such as post-stroke upper and lower limb spasticity, dystonia, hemifacial spasm, a sequela after a cerebrovascular disease and cosmetic surgery.

In the *botulinum* preparation, a pharmaceutically acceptable additional ingredient may be contained in addition to the purified *botulinum* toxin that is an active ingredient. Examples of the additional ingredient include an excipient, a stabilizing agent and a buffering agent. Examples of the excipient include sucrose, trehalose, lactose and a polysaccharide, preferably sucrose. Examples of the stabilizing agent include human serum albumin, recombinant human serum albumin, caprylic acid, acetyltryptophan, sodium chloride, polysorbate 80, octanoic acid and arginine (L-arginine hydrochloride), preferably recombinant human serum albumin and L-arginine hydrochloride. Examples of the buffering agent include sodium dihydrogen phosphate dihydrate and disodium hydrogen phosphate hydrate. Among these additional ingredients, one component or a combination of a plurality of components may be used.

The dosage form of the *botulinum* preparation is not particularly limited, and may be a liquid form or a solid form. A solid *botulinum* preparation may be a freeze-dried product, a vacuum-dried product or a spray-dried product of a liquid preparation, and can be dissolved in saline or water upon use to reconstitute the solid *botulinum* preparation into a liquid preparation.

EXAMPLES

Hereinbelow, the present invention will be described in detail with reference to examples and comparative examples. However, the present invention is not limited to these examples.

Test Example 1

[1] Production of *botulinum* Toxin

Example 1

A *botulinum* toxin was produced in the following manner.
(A) Production of *botulinum* Bacterium
A preculture step including static culture 1 and static culture 2 and a main culture step including a bacterial growth stage by agitation culture and a fermentation stage were carried out. That is, the preculture step and the bacterial growth stage (A1) in the main culture step were carried out, and then the fermentation stage (A2) in the main culture step was carried out.

In the static culture 1, 0.5 mL of seed cells, which had been produced from an infant botulism pathogenic bacterium Chiba-H (a type-A2 *botulinum* bacterium Chiba-H strain) in the form of spores, were seeded in 20 mL of a culture medium which had contained Bacto Proteose Peptone No. 3 (pork peptone, Becton, Dickinson and Company) (final concentration: 8 w/v %), yeast extract (final concentration: 1 w/v %), sodium thioglycolate (final concentration: 0.025 w/v %) and glucose (final concentration: 0.5 w/v %) and was adjusted to pH 7.3, and were then cultured at 35° C. until the OD660 value became 0.5 or more. In the static culture 2, 20 mL of a culture produced in the static culture 1 was seeded in 400 mL of a culture medium consist of the same composition and the same pH as those used in static culture 1, and was then cultured at 35° C. until the OD660 value became 2.5 or more.

In the bacterial growth stage in the main culture step, about 150 mL of a culture produced in the static culture 2 was seeded in 10 L of a culture medium which had contained Bacto Proteose Peptone No. 3 (pork peptone, Becton, Dickinson and Company) (final concentration: 2 w/v %), yeast extract (final concentration: 1 w/v %), sodium thioglycolate (final concentration: 0.025 w/v %) and glucose (final concentration: 0.5 w/v %) and had been adjusted to pH 7.3. The culture was then cultured at 35° C. while agitating under a nitrogen gas atmosphere. Then, 1 mol/L of HCl was added to the culture after the proliferation of the cells reached the peak thereof to decrease the pH of the culture medium to 5.8, and then the fermentation stage was carried out. In the fermentation stage, the pH of the culture medium was maintained at 5.8 by adding 1 mol/L of HCl as required until the culturing was completed. The time required for the main culture step was about 44 hours.

(B) Removal of Bacterial Component

The culture produced by the main culture step was filtered and then concentrated by the following filters and membranes. The filter filtration was carried out by passing the culture obtained from the main culture step through a filter 1 [3M Company, Zeta-plus filter (05SP)/1020 cm$^2$; pore diameter: corresponding to about 1.0 to 10 μm], a filter 2 [3M Company, Zeta-plus filter maximizer (60SP03A)/1020 cm$^2$; pore diameter: corresponding to about 0.1 to 1.0 μm] and a filter 3 [Sartorius AG, Sartopore 2 pore diameter: 0.45 μm+0.2 μm)/0.1 m$^2$] in this order. A filtrate obtained by the membrane filtration was concentrated by a membrane that has a pore diameter (molecular weight cut-off) of 30 KDa (Sartorius AG, Sartocon Slice Hydrosart 30 kD) and by a 20-mmol/L phosphate buffer (pH 6.0) containing 0.1 mol/L of NaCl and 20 mmol/L of citric acid. A membrane liquid concentrate (0.9 L) thus obtained is also referred to as a "harvest solution 11", hereinafter. Subsequently, a half (0.45 L) of the total volume (0.9 L) was subjected to membrane concentration using a 10-mmol/L phosphate buffer (pH 6.0) and a membrane having a pore diameter (molecular weight cut-off) of 30 KDa (Sartorius AG, Sartocon Slice Hydrosart 30 kD). A membrane liquid concentrate thus obtained is also referred to as a "harvest solution 12", hereinafter.

(C) Treatment With Endonuclease $MgCl_2$ and Benzonase (Merck KGaA, registered trademark) were added at final concentrations of 1 mmol/L and 20 U/mL, respectively, to the harvest solution 12, and the resultant solution was treated at 30° C. for about 15 hours while stirring under the condition of pH 6.0. The number of times for adding benzonase was once. Subsequently, an endonuclease-treated product was filtrated by Zeta Plus Encapsulated Filter manufactured by 3M Company.

(D) Removal of Nucleic Acid Degradation Product

A filtrate thus obtained was subjected to membrane concentration using a 10-mmol/L phosphate buffer (pH 6.0) and a membrane having a pore diameter (molecular weight cut-off) of 30 KDa (Sartorius AG, Sartocon Slice Hydrosart 30 kD) to remove a nucleic acid degradation product. For the removal of the nucleic acid degradation product by the membrane, tangential flow filtration was employed. In this manner, a membrane liquid concentrate was obtained.

The membrane liquid concentrate was subjected to membrane concentration using 50 mmol/L of sodium acetate (pH 4.2) containing 0.2 mol/L of NaCl and a membrane (Sartorius AG, Sartocon Slice Hydrosart 30 kD) having a pore diameter (molecular weight cut-off) of 30 KDa. A membrane liquid concentrate thus obtained is also referred to as an "isolated *botulinum* toxin liquid 1", hereinafter.

(E) Purification of Complexed *botulinum* Toxin

The isolated *botulinum* toxin liquid 1 was subjected to cation exchange chromatography. As a cation exchanger, SP-Sepharose-fast flow was used and was packed in a length of 30 cm in a column having a size of 70×550 mm The column was equilibrated by 50 mmol/L of sodium acetate (pH 4.2) containing 0.2 mol/L of NaCl as a washing solution, then the isolated *botulinum* toxin liquid 1 was applied to the column, and then the column was eluted by 50 mmol/L of sodium acetate (pH 4.2) containing 0.7 mol/L of NaCl as an eluate under a gradient condition of 8 column volumes to 0.7 mol/L of NaCl. The flow rate was about 15 mL/min An eluate thus obtained was subjected to membrane concentration using a 50-mmol/L acetate buffer (pH 6.0) containing 0.2 mol/L of NaCl and a membrane having a pore diameter (molecular weight cut-off) of 30 KDa (Sartorius AG, Sartocon Slice Hydrosart 30 kD) to produce a concentrated solution, and the concentrated solution was filtrated by a filter having a pore diameter of 0.22 μm (Corning Incorporated, a bottle-top filter, made from PES) to produce a purification product of a complexed *botulinum* toxin (M toxin).

(F) Purification of Non-Complexed *botulinum* Toxin

The purification product of the complexed *botulinum* toxin (M toxin) thus obtained was subjected to membrane concentration using a 10-mmol/L phosphate buffer (pH 7.5) and membranes each having a pore diameter (molecular weight cut-off) of 10 KDa (Sartorius AG, Sartocon Slice 50 Hydrosart 10 kD; and Millipore, Pellicon XL Ultracel 10 kD). Subsequently, a membrane concentrate thus obtained was subjected to anion exchange column chromatography. As an anion exchanger, DEAE-Sepharose-fast flow which was a weak anion exchanger was used, and the exchanger was packed in a length of 30 cm in a column having a size of 10×450 mm The column was equilibrated by a 10-mmol/L phosphate buffer (pH 7.5) as a washing solution, then the membrane concentrate was applied to the column, and then the column was eluted by a 10-mmol/L phosphate buffer (pH 7.5) containing 0.3 mol/L of NaCl as an eluate under a gradient condition of 10 column volumes to 0.3 mol/L of NaCl. The flow rate was about 1 mL/min. An eluate thus obtained was filtrated using a filter having a pore diameter of 0.22 μm (Starlab, a PES-made syringe filter), then a preservative agent (L-arginine hydrochloride) was added thereto at a final concentration of 1 w/v % to produce a purification product of a non-complexed *botulinum* toxin (S toxin) (which is also referred to as an "S toxin purification product 1", hereinafter).

Comparative Example 1

The same procedure as in Example 1 was carried out, except that the steps (C) and (D) are replaced by the following method. In this manner, a purification product of a non-complexed *botulinum* toxin (S toxin) was produced. More specifically, the below-mentioned anion exchange chromatography, membrane concentration and filtration were carried out using the remaining half volume (0.45 L) of the harvest solution 11 (the filter filtrate) obtained in the step (B) in Example 1, and then the steps (E) and (F) in Example 1 were carried out.

The harvest solution 11 was subjected to anion exchange chromatography. As an anion exchanger, Qsepharose-fast flow was used and was packed in a length of 10 cm in a column having a size of 140×500 mm The column was equilibrated by a 20-mmol/L phosphate buffer (pH 6.0) containing 0.1 mol/L of NaCl and 20 mmol/L of citric acid as a washing solution, then the harvest solution 11 obtained in the step (B) in Example 1 was applied to the column, and then the same washing solution was passed through the column at a flow rate of about 150 mL/min In this manner, a toxin fraction was collected as a pass-through fraction without the need to adsorb the toxin fraction onto the column. A collected solution was subjected to membrane concentration using 50 mmol/L of sodium acetate (pH 4.2) containing 0.2 mol/of NaCl and a membrane having a pore diameter (molecular weight cut-off) of 30 KDa (Sartocon Slice Hydrosart 30 kD). A membrane liquid concentrate thus obtained is also referred to as an "isolated *botulinum* toxin liquid 1'''", hereinafter. The same procedure as in the steps (E) and (F) in Example 1 was carried out to produce a purification product of a non-complexed *botulinum* toxin (S toxin) (also referred to as an "S toxin purification product 1'''", hereinafter) was produced.

[2] Confirmation of Purification

Figure 1:
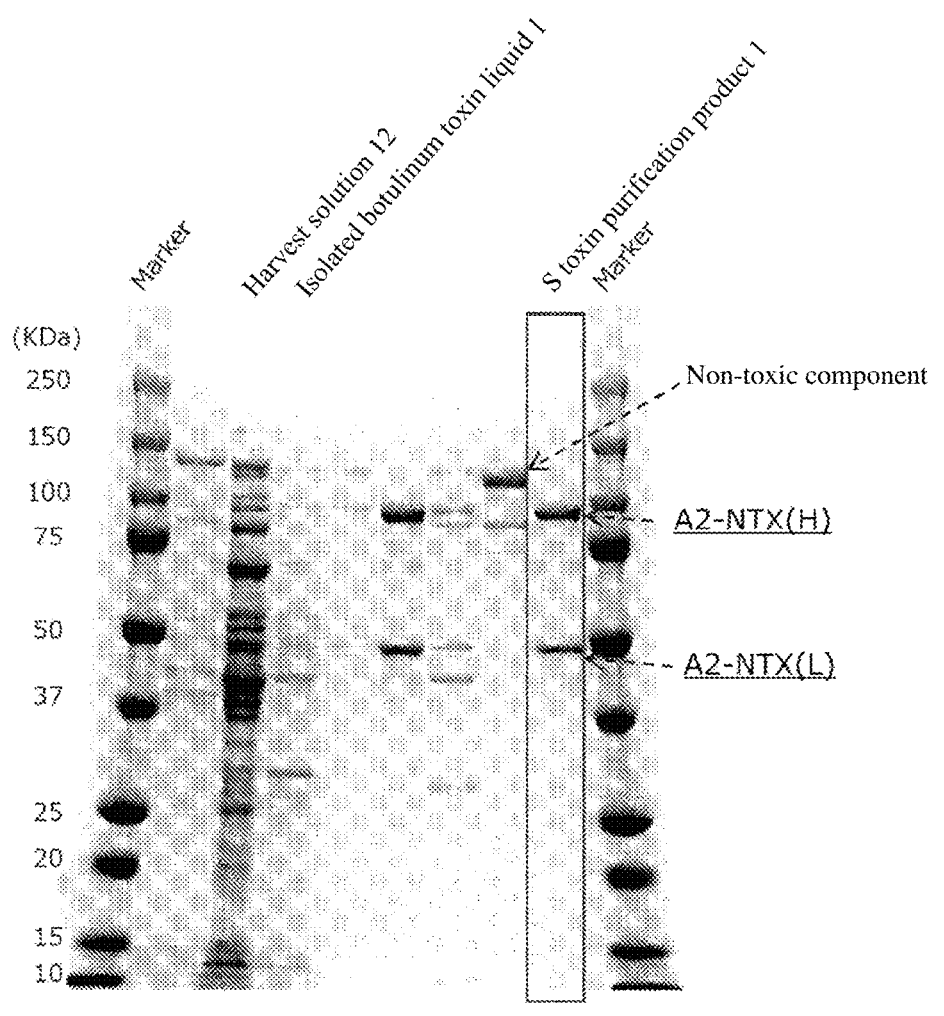

With respect to Example 1, each of the harvest solution 12, the isolated *botulinum* toxin liquid 1 and the S toxin purification product 1 was developed on SDS-PAGE. With respect to Comparative Example 1, each of the harvest solution 11, the isolated *botulinum* toxin liquid 1' and the S toxin purification product 1' was developed on SDS-PAGE. The staining with CBB was carried out to confirm the success of purification of a *botulinum* toxin. The stained gels are shown in FIG. 1 (Example 1) and FIG. 2 (Comparative Example 1). In the figures, "A2-NTX(H)" indicates a heavy chain of about 100 KDa, and "A2-NTX(L)" indicates a light chain of about 50 KDa.

Figure 2:
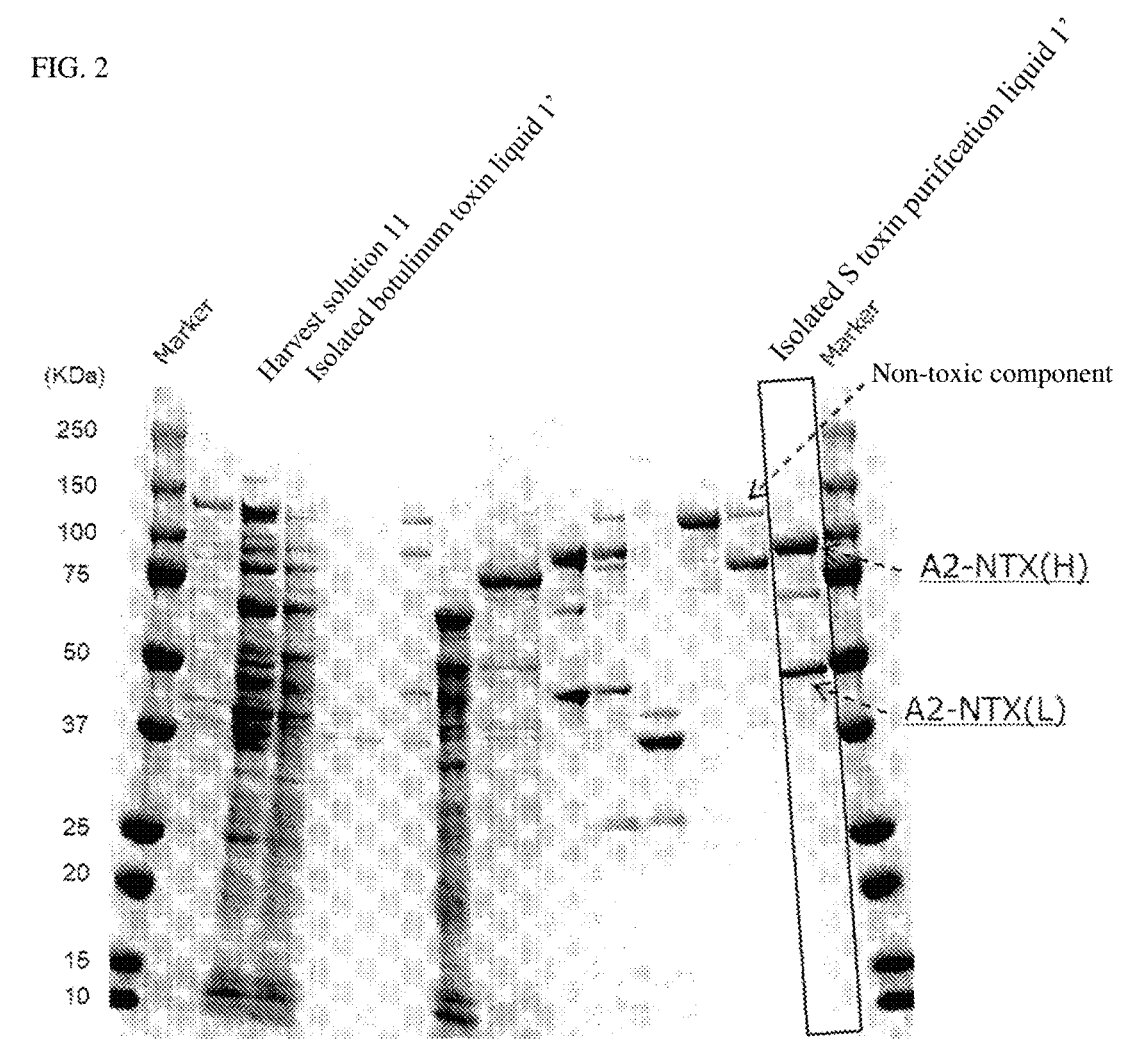

In FIG. 1, a lane located immediately to the right of the markers indicates a culture supernatant of the main culture solution, and lanes located between the isolated *botulinum* toxin liquid 1 and the S toxin purification product 1 indicate the purification product of the complexed *botulinum* toxin (M toxin), a toxin-contained solution obtained after the DEAE chromatography, an impurity solution 1 obtained after the DEAE chromatography, and an impurity solution 2 obtained after the DEAE chromatography in this order as observed from the left. In FIG. 2, a lane located immediately to the right of the markers indicates a culture supernatant of the main culture solution, and lanes located between the isolated *botulinum* toxin liquid 1' and the S toxin purification product 1' indicate an impurity solution obtained after the anion exchange chromatography, the purification product of the complexed *botulinum* toxin (M toxin), an impurity solution 1 obtained after the cation exchange chromatography, an impurity solution 2 obtained after the cation exchange chromatography, a toxin-containing solution obtained after the DEAE chromatography, an impurity solution 1 obtained after the DEAE chromatography, an impurity solution 2 obtained after the DEAE chromatography, an impurity solution 3 obtained after the DEAE chromatography, and an impurity solution 4 obtained after the DEAE chromatography in this order as observed from the left.

As shown in the comparison between FIGS. 1 and 2, it was demonstrated that impurities each having a molecular weight of about 75 kDa still remained in Comparative Example 1, while almost all of the impurities were removed in Example 1.

[3] Measurement of Purification Efficiency

A purification efficiency by a nucleic acid removal operation was measured. More specifically, the purification efficiency in Example 1 was determined by calculating the ratio (%) of the amount of nucleic acid in the isolated *botulinum* toxin liquid 1 obtained in the step (D) to that in the harvest solution 12 (membrane liquid concentrate) obtained in the step (B) and then subtracting the ratio from 100%. The purification efficiency in Comparative Example 1 was determined by calculating the ratio of the amount of nucleic acid in the isolated *botulinum* toxin liquid 1' to that in the harvest solution 11 (filter filtrate) obtained in the step (B) and then subtracting the ratio from 100%.

Purification efficiency by nucleic acid removal operation in Example 1=100−{(amount of nucleic acid in isolated *botulinum* toxin liquid 1/amount of nucleic acid in harvest solution 12)×100}

Purification efficiency by nucleic acid removal operation in Comparative Example 1=100−{ (amount of nucleic acid in isolated *botulinum* toxin liquid 1'/amount of nucleic acid in harvest solution 11)×100}   [Mathematical formula 1]

The amount of nucleic acid was determined as the sum total of the amount of DNA determined with ds DNA HS Assay Kit using Qubit3.0 fluorometer (Thermo Fisher Scientific K.K.) and the amount of RNA determined with RNA HS Assay Kit using the same device.

As a result, the amount of nucleic acid in the isolated *botulinum* toxin liquid 1' was about two folds the amount of nucleic acid in the isolated *botulinum* toxin liquid 1. Consequently, significantly high purification efficiency was achieved by the nucleic acid removal operation in Example 1 compared with the nucleic acid removal operation in Comparative Example 1.

[4] Measurement of Yield of *botulinum* Toxin

The yield of a *botulinum* toxin by a nucleic acid removal operation was measured. More specifically, the *botulinum* toxin yield in Example 1 was calculated as a ratio of the total toxin amount in the isolated *botulinum* toxin liquid 1 obtained in the step (D) to that in the harvest solution 12 (membrane liquid concentrate) obtained in the step (B), and the *botulinum* toxin yield in Comparative Example 1 was calculated as a ratio of the total toxin amount in the isolated *botulinum* toxin liquid 1' to that in the harvest solution 11 (filter filtrate) obtained in the step (B).

Toxin yield by nucleic acid removal operation in Example 1=(total toxin amount in isolated *botulinum* toxin liquid 1/total toxin amount in harvest solution 12)×100

Toxin yield by nucleic acid removal operation in Comparative Example 1=(total toxin amount in isolated *botulinum* toxin liquid 1'/total toxin amount in harvest solution 11)×100   [Mathematical formula 2]

The total toxin amount was determined as a value expressed in the unit U (1 U=1 LD50) by carrying out the preparation of a sample and the inoculation of the sample to a mouse by using each of the harvest solution 11, the harvest solution 12, the isolated *botulinum* toxin liquid 1 and the isolated *botulinum* toxin liquid 1' in accordance with the below-mentioned titer measurement method.

As a result, the toxin yield by a nucleic acid removal operation in Example 1 was 53.18% and the toxin yield by a nucleic acid removal operation in Comparative Example 1 was 50.46%. The toxin yield in Example 1 was higher compared with that in Comparative Example 1.

[5] Measurement of *botulinum* Toxin

The titer, which was expressed in the unit U/mL, was determined in the following manner.

The S toxin purification product was diluted appropriately, was then inoculated at a dose of 0.1 mL per mouse from a tail vein of the mouse, and then the survival time of the mouse was confirmed. The LD50 value (U/mL) per 1 mL of the S toxin purification product was calculated from a regression line of the previously validated survival time and the LD50 value in the case of intraperitoneal administration. The mass (mg/mL) of a protein per 1 mL of the S toxin purification product was determined from the absorption of infrared ray having a wavelength of 280 nm. The LD50 value (U/mL) per 1 mL of the S toxin purification product was divided by the mass of (mg/mL) of a protein per 1 mL of the S toxin purification product to produce a specific activity (U/mg).

As a result, the specific activity of the S toxin purification product 1 obtained in Example 1 was $8.21 \times 10^7$ U/mg, and the specific activity of the S toxin purification product obtained in Comparative Example 1 was $2.59 \times 10^7$ U/mg. Thus, in Example 1, a purification product having a higher specific activity was produced compared with Comparative Example 1.

Test Example 2

[1] Production of *botulinum* Toxin

Example 2

In this example, the same procedure as in Example 1 was carried out, except that an animal-free culture medium was used in the step of producing a *botulinum* toxin and Denarase was used as the endonuclease which were the primary changes. In this manner, a *botulinum* toxin was produced. More specifically, a *botulinum* toxin was produced in the following manner.

(A) Production of *botulinum* Bacterium

A *botulinum* bacterium was produced in the same manner as in Example 1, except that Vegetable Peptone No. 1 (a vegetable peptone, Thermo Fisher Scientific K.K.) was used as a culture medium in the preculture step and the main culture step and the culture amount in the preculture step (including the static culture 1 and the static culture 2) was reduced to half and about 10 mL of a culture obtained in the static culture 1 was seeded in a culture medium in the static culture 2.

(B) Removal of Bacterial Component

The culture produced by the main culture step was filtered and then concentrated by the following filters and membranes. The filter filtration was carried out by passing the culture obtained from the main culture step through a filter 1 [3M Company, Zeta-plus filter (05SP)/1020 cm²; pore diameter: corresponding to about 1.0 to 10 μm], a filter 2 [3M Company, Zeta-plus filter maximizer (60SP03A)/1020 cm²; pore diameter: corresponding to about 0.1 to 1.0 μm] and a filter 3 [Sartorius AG, Sartopore 2 pore diameter: 0.45 μm+0.2 μm)/0.1 m²] in this order. A filtrate obtained by the membrane filtration was concentrated by a membrane that has a pore diameter (molecular weight cut-off) of 30 KDa (Sartorius AG, Sartocon Slice Hydrosart 30 kD) and by a 20-mmol/L phosphate buffer (pH 6.0) containing 0.1 mol/L of NaCl and 20 mmol/L of citric acid. Subsequently, the resultant solution was subjected to membrane concentration using a 10-mmol/L phosphate buffer (pH 6.0) and a membrane having a pore diameter (molecular weight cut-off) of 30 KDa (Sartorius AG, Sartocon Slice Hydrosart 30 kD). A membrane liquid concentrate produced in this manner is also referred to as a "harvest solution 22", hereinafter.

(C) Treatment With Endonuclease

The endonuclease treatment and filtration were carried out in the same manner as in Example 1, except that Denarase (c-LEcta GmbH, registered trademark) was used as the endonuclease and the treatment time was about 19 hours. In this manner, a filtrate was produced.

(D) Removal of Nucleic Acid Degradation Product

The filtrate thus obtained was subjected to membrane filtration for about 1 hour using a 10-mmol/L phosphate buffer (pH 6.0) and a membrane having a pore diameter (molecular weight cut-off) of 30 KDa (Sartorius AG, Sartocon Slice Hydrosart 30 kD) to remove a nucleic acid degradation product. For the removal of the nucleic acid degradation product by the membrane, tangential flow filtration was employed. In this manner, a membrane liquid concentrate was obtained. The membrane liquid concentrate was subjected to membrane concentration for about 20 minutes using 50 mmol/L of sodium acetate (pH 4.2) containing 0.2 mol/L of NaCl and a membrane having a pore diameter (molecular weight cut-off) of 30 kDa (Sartorius AG, Sartocon Slice Hydrosart 30 kD). A membrane liquid concentrate thus obtained is also referred to as an "isolated *botulinum* toxin liquid 2", hereinafter.

(E) Purification of Complexed *botulinum* Toxin

The isolated *botulinum* toxin liquid 2 was subjected to cation exchange chromatography in the same manner as in Example 1. An eluate thus obtained was subjected to membrane concentration using a 50-mmol/L acetate buffer (pH 6.0) containing 0.2 mol/L of NaCl and a membrane having a pore diameter (molecular weight cut-off) of 30 KDa (Sartorius AG, Sartocon Slice Hydrosart 30 kD) and was then filtrated using a filter having a pore diameter of 0.22 μm (Corning Incorporated, a bottle-top filter, made from PES) to produce a purification product of a complexed *botulinum* toxin (M toxin).

(F) Purification of Non-Complexed *botulinum* Toxin

A purification product of a non-complexed *botulinum* toxin (S toxin) (also referred to as an "S toxin purification product 2", hereinafter) was produced in the same manner as in Example 1 from the purification product of the complexed *botulinum* toxin (M toxin).

Example 3

In this example, the same procedure as in Example 1 was carried out, except that static culture was carried out in the main culture step in the *botulinum* toxin production step and the addition of an endonuclease was carried out twice which were the primary changes. In this manner, a *botulinum* toxin was produced. More specifically, a *botulinum* toxin was produced in the following manner.

(A) Production of *botulinum* Bacterium

The preculture step (static culture 1 and static culture 2) was carried out in the same manner as in Example 1, except that 0.4 mL of seed cells were seeded, the culture amount in the static culture 1 was changed to 10 mL, the culture amount in the static culture 2 was changed to 250 mL and about 10 mL of a culture obtained by the static culture 1 was seeded in a culture medium for the static culture 2. In the bacterial growth stage in the main culture step, about 150 mL of a culture produced by the static culture 2 was seeded in 10 L of a culture medium which had contained Bacto Proteose Peptone No. 3 (pork peptone, Becton, Dickinson and Company) (final concentration: 2 w/v %), yeast extract (final concentration: 1 w/v %), sodium thioglycolate (final concentration: 0.025 w/v %) and glucose (final concentration: 1.0 w/v %) and had been adjusted to pH 7.3. The culture was then subjected to static culture at 35° C. under a hermetically shielded condition, and the static culture was shifted to the fermentation stage spontaneously without the need to adjust the pH. The time required for the main culture step was about 44 hours, and the pH of the culture medium at the time point of the completion of the culturing was about 6.0.

(B) Removal of Bacterial Component

A culture obtained by the main culture step was subjected to the same procedure as in Example 1, except that membrane concentration using a 20-mmol/L phosphate buffer (pH 6.0) containing 0.1 mol/L of NaCl and 20 mmol/L of citric acid and a membrane having a pore diameter (molecular weight cut-off) of 30 KDa (Sartorius AG, Sartocon Slice Hydrosart 30 kD) was not carried out. In this manner, a harvest solution 32 corresponding to the harvest solution 12 was produced.

(C) Treatment With Endonuclease $MgCl_2$ and Benzonase were added at final concentrations of 1 mmol/L and 50 U/mL (for the addition in a first-round), respectively, to the harvest solution 32, and the resultant solution was allowed to react at 30° C. for about 5 hours while stirring under the condition of pH 6.0. Subsequently, 50 U/mL (for the addition in a second round) of Benzonase was further added to the solution in such a manner that the total amount of Benzonase added in the first and second rounds became 100 U/mL, and the resultant solution was further allowed to react for about 12 hours (about 13 hours in total). Subsequently, an endonuclease-treated product was filtered by Zeta Plus Encapsulated Filter manufactured by 3M Company.

(D) Removal of Nucleic Acid Degradation Product

A filtrate thus obtained was subjected to membrane concentration using a 50-mmol/L acetate buffer (pH 4.2) containing 0.2 mol/L of NaCl and a membrane having a pore diameter (molecular weight cut-off) of 30 KDa (Sartorius AG, Sartocon Slice Hydrosart 30 kD) to remove a nucleic acid degradation product. For the removal of the nucleic acid degradation product with the membrane, tangential flow filtration was employed. A membrane liquid concentrate thus obtained is also referred to as an "isolated *botulinum* toxin liquid 3", hereinafter.

(E) Purification of Complexed *botulinum* Toxin

The isolated *botulinum* toxin liquid 3 was subjected to cation exchange chromatography in the same manner as in Example 1. The elution was carried out using a 50-mmol/L sodium acetate (pH 4.2) containing 0.7 mol/L of NaCl as an eluate under a gradient condition of 8 column volumes to 0.7 mol/L of NaCl. An eluate thus obtained was subjected to membrane concentration using a 10-mmol/L phosphate buffer (pH 7.5) and a membrane having a pore diameter (molecular weight cut-off) of 10 KDa (Sartorius AG, Sartocon Slice 50 Hydrosart 10 kD) to produce a purification product of a complexed *botulinum* toxin (M toxin).

(F) Purification of Non-Complexed *botulinum* Toxin

The purification product of the complexed *botulinum* toxin (M toxin) was subjected to membrane concentration using a 10-mmol/L phosphate buffer (pH 7.5) and a membrane having a pore diameter (molecular weight cut-off) of 10 KDa (Millipore, Pellicon XL Ultracel 10 kD), and was then subjected to anion exchange column chromatography. As an anion exchanger, DEAE-Sepharose-fast flow which was a weak anion exchanger was used, and the exchanger was packed in a length of 30 cm in a column having a size of 10×450 mm The column was equilibrated by a 10-mmol/L phosphate buffer (pH 7.5) as a washing solution, then the purification product of the complexed *botulinum* toxin (M toxin) was applied to the column, and then the column was eluted by a 10-mmol/L phosphate buffer (pH 7.5) containing 0.3 mol/L of NaCl as an eluate under a gradient condition of 10 column volumes to 0.3 mol/L of NaCl. The flow rate was about 1 mL/min. A preservative agent (L-arginine hydrochloride) was added at a final concentration of 1 w/v % to an eluate thus produced, and then the resultant solution was filtrated using a filter having a pore diameter of 0.22 μm (Starlab, a PES-made syringe filter) to produce a purification product of a non-complexed *botulinum* toxin (S toxin) (which is also referred to as an "S toxin purification product 3", hereinafter).

Confirmation of Purification

Figure 3:
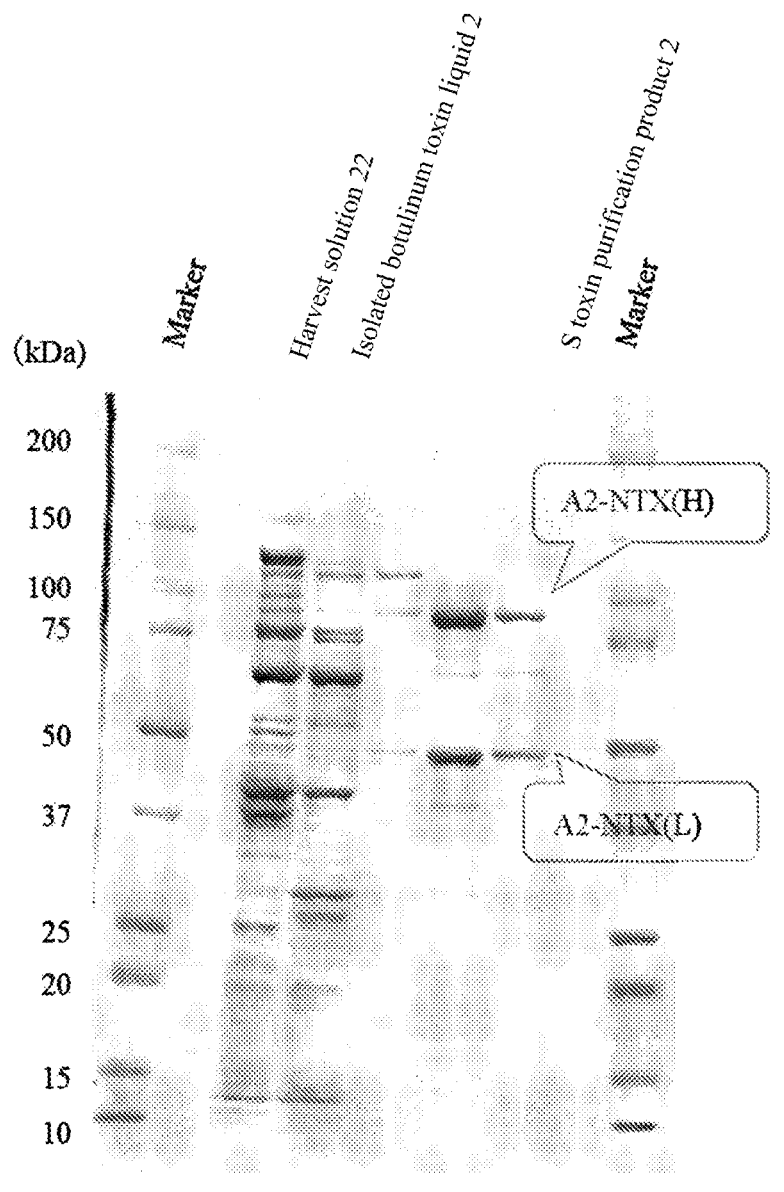

With respect to Example 2, each of the harvest solution 22, the isolated *botulinum* toxin liquid 2 and the S toxin purification product 2 was developed on SDS-PAGE. With respect to Example 3, each of the harvest solution 32, the isolated *botulinum* toxin liquid 3 and the S toxin purification product 3 was developed on SDS-PAGE. The staining with CBB was carried out to confirm the success of purification of a *botulinum* toxin. The SDS-PAGE and the staining method were the same as those used in Test Example 1. The stained gels thus obtained are shown in FIG. 3 (Example 2) and FIG. 4 (Example 3). In the figures, "A2-NTX(H)" indicates a heavy chain of about 100 KDa, and "A2-NTX (L)" indicates a light chain of about 50 KDa.

Figure 4:
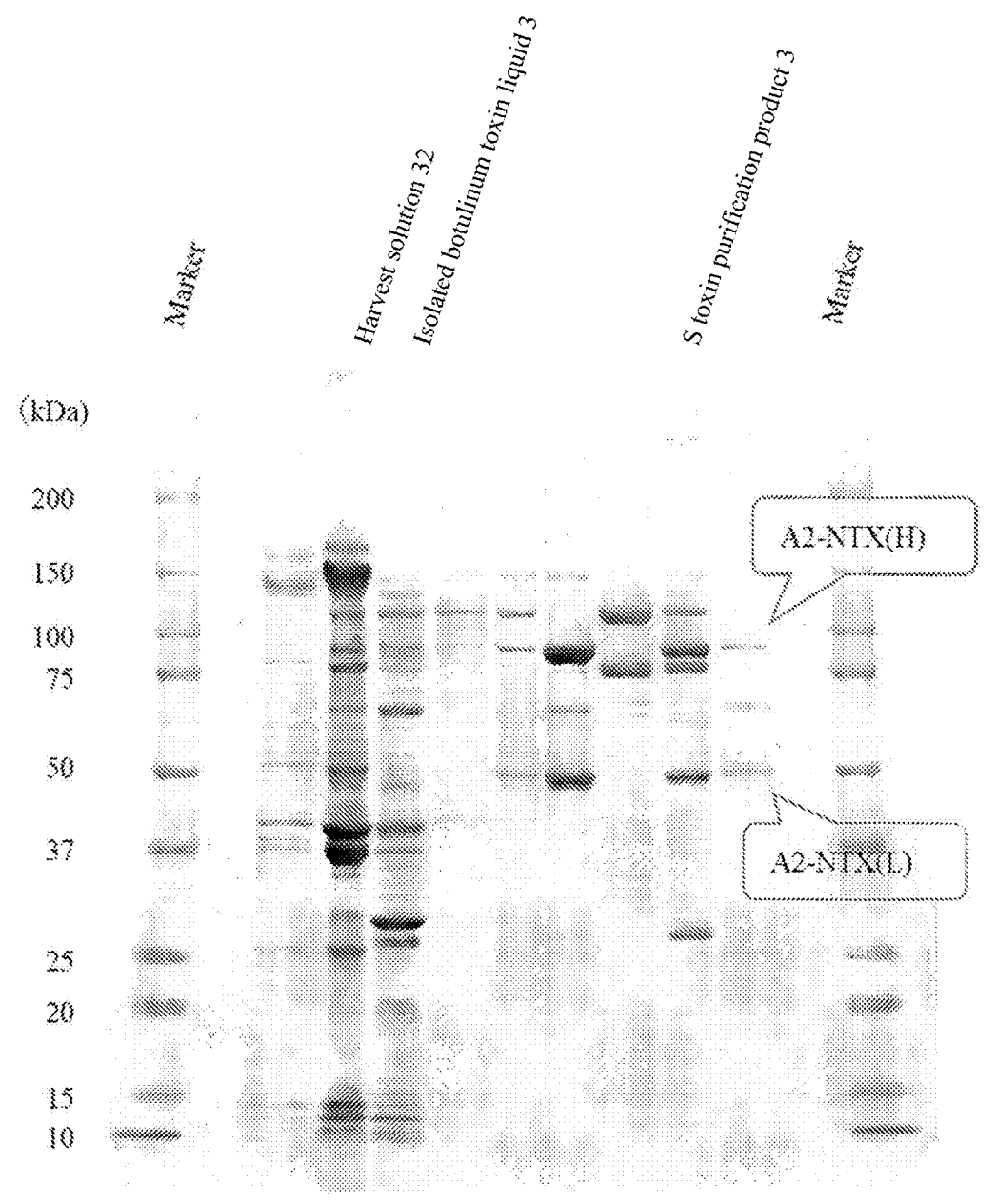

In FIG. 3, lanes located between the isolated *botulinum* toxin liquid 2 and the S toxin purification product 2 indicate the purification product of the complexed *botulinum* toxin (M toxin) and a toxin-containing solution obtained after the DEAE chromatography in this order as observed from the left. In FIG. 4, a lane located immediately to the left of the harvest solution 32 indicates a culture supernatant of the main culture solution, and lanes located between the isolated *botulinum* toxin liquid 3 and the S toxin purification product 3 indicate a toxin-containing solution obtained after the SP chromatography, the purification product of the complexed *botulinum* toxin (M toxin), a toxin-containing solution obtained after the DEAE chromatography, an impurity solution 1 obtained after the DEAE chromatography, and an impurity solution 2 obtained after the DEAE chromatography in this order as observed from the left.

As shown in FIGS. 3 and 4, almost all of impurities were removed in both of Examples 2 and 3.

[3] Measurement of Yield of *botulinum* Toxin

The yield of a *botulinum* toxin by a nucleic acid removal operation was measured. More specifically, the *botulinum* toxin yield in each of Examples 2 and 3 was calculated as the ratio of the total toxin amount in each of the isolated *botulinum* toxin liquids 2 and 3 obtained in the step (D) to the total toxin amount in each of the harvest solutions 22 and 32 (membrane liquid concentrates) obtained in the step (B).

Toxin yield by nucleic acid removal operation in Example 2=(total toxin amount in isolated *botulinum* toxin liquid 2/total toxin amount in harvest solution 22)×100

Toxin yield by nucleic acid removal operation in Example 3=(total toxin amount in isolated *botulinum* toxin liquid 3/total toxin amount in harvest solution 32)×100  [Mathematical formula 3]

For the determination of each of the total toxin amounts, the preparation of a sample and the inoculation of the sample to a mouse were carried out using each of the harvest solutions 22 and 32 and the isolated *botulinum* toxin liquids 2 and 3 in accordance with the above-mentioned titer measurement method, and the total toxin amount was obtained as a value expressed in the unit U (1 U=1 LD50).

As a result, the toxin yield by the nucleic acid removal operation in Example 2 was 59.71% and the toxin yield by the nucleic acid removal operation in Example 3 was 89.68%.

[4] Measurement of *botulinum* Toxin

The specific activity of each of the *botulinum* toxins (i.e., the S toxin purification products 2 and 3) was determined in the same manner as in Test Example 1, except that the content of a protein was measured by BCA method. As a result, the specific activity of the S toxin purification product 2 obtained in Example 2 was $10.06 \times 10^7$ U/mg, and the specific activity of the S toxin purification product 3 obtained in Example 3 was $6.46 \times 10^7$ U/mg.

The invention claimed is:

1. A method for producing a botulinum toxin, comprising steps of:
    (A) producing a botulinum toxin from a botulinum toxin-producing bacterium in a culture medium to produce a mixture a containing a bacterial component and a nucleic acid component both derived from the botulinum toxin and the botulinum toxin;
    (B) subjecting the mixture a to a removal of the bacterial component to produce a mixture b containing the nucleic acid component and the botulinum toxin;
    (C) adding an endonuclease to the mixture b to produce a mixture c containing a nucleic acid degradation product and the botulinum toxin; and
    (D) subjecting the mixture c to a removal of the nucleic acid degradation product to produce an isolated botulinum toxin liquid d,
    wherein the method excludes any acid precipitation step.

2. The method for producing a botulinum toxin according to claim 1, wherein, in the step (C), the endonuclease is an endonuclease derived from a *Serratia* bacterium *Serratia marcescens*.

3. The method for producing a botulinum toxin according to claim 1, wherein the step (C) is carried out under a condition of pH 5.8 to 6.5.

4. The method for producing a botulinum toxin according to claim 1, wherein, in the step (C), the endonuclease is added a plurality of times.

5. The method for producing a botulinum toxin according to claim 1, wherein, in the step (D), the removal of the nucleic acid degradation product includes a removal using a membrane.

6. The method for producing a botulinum toxin according to claim 1, wherein the method further includes a step (E) of subjecting the isolated botulinum toxin liquid d to cation exchange chromatography to produce a purification product of a complexed botulinum toxin.

7. The method for producing a botulinum toxin according to claim 6, wherein the method further includes a step (F) of subjecting the purification product of the complexed botulinum toxin to anion exchange chromatography under a condition where a non-toxic non-HA protein can be dissociated from the complexed botulinum toxin to produce a purification product of a non-complexed botulinum toxin.

8. The method for producing a botulinum toxin according to claim 1, wherein at least the step (A) includes a preculture step and a main culture step and at least the preculture step is carried out by static culture.

9. The method for producing a botulinum toxin according to claim 8, wherein both of the preculture step and the main culture step are carried out by static culture.

10. The method for producing a botulinum toxin according to claim 8, wherein the step (A) includes following steps in this order:

(A1) carrying out a bacterial growth of the botulinum toxin-producing bacterium in a culture medium of pH 6.8 to 8.0; and (A2) carrying out a fermentation of the botulinum toxin-producing bacterium in a culture medium of pH 5.0 to 6.5.

11. The method for producing a botulinum toxin according to claim 1, wherein, in the step (A), the botulinum toxin-producing bacterium is a germinated body of a cell which is stored in a form of a spore.

12. The method for producing a botulinum toxin according to claim 1, wherein, in the step (B), the removal of the bacterial component includes filter filtration.

13. The method for producing a botulinum toxin according to claim 7, wherein, in the step (F), the condition includes pH 7.3 to 8.5.

14. The method for producing a botulinum toxin according to claim 7, wherein, in the step (F), the anion exchange chromatography is weak anion exchange chromatography.

* * * * *